United States Patent [19]

Angstadt et al.

[11] Patent Number: 5,212,136
[45] Date of Patent: May 18, 1993

[54] SOLID-ACID ALKYLATION CATALYST COMPOSITIONS FOR ALKYLATION PROCESSES

[75] Inventors: Howard P. Angstadt, Media, Pa.; Elmer J. Hollstein, Wilmington, Del.; Chao-Yang Hsu, Media, Pa.

[73] Assignee: Sun Company, Inc (R&M), Philadelphia, Pa.

[21] Appl. No.: 800,797

[22] Filed: Nov. 27, 1991

[51] Int. Cl.$^5$ ............................. B01J 27/053
[52] U.S. Cl. ............................. 502/206; 502/217; 585/709
[58] Field of Search ................ 502/217, 206; 585/709

[56] References Cited

U.S. PATENT DOCUMENTS 3,032,599  5/1962  Holm et al. ................ 502/217

*Primary Examiner*—W. J. Shine
*Attorney, Agent, or Firm*—Q. Todd Dickinson; Donald R. Johnson

[57] ABSTRACT

New catalyst compositions comprise sulfated and calcined mixtures of (1) a support comprising an oxide or hydroxide of a Group IV-A element, (2) an oxide or hydroxide of molybdenum, and (3) an oxide or hydroxide of a Group I-B, II-B, III-A, III-B, IV-B, V-A or VI-A metal other than molybdenum or a metal of the Lanthanide Series of the Periodic Table. A process for alkylation of acyclic saturated compounds with acyclic unsaturated compounds utilizing such catalyst compositions.

9 Claims, No Drawings

SOLID-ACID ALKYLATION CATALYST COMPOSITIONS FOR ALKYLATION PROCESSES

The reaction of isobutane with low ($C_2$–$C_5$) molecular weight olefins to produce $C_6$–$C_9$ paraffins is commonly referred to as alkylation. In commercial practice this reaction is carried out in the presence of acid type catalysts such as concentrated sulfuric acid or HF. The reaction is an important process in the petroleum industry as it represents a means to upgrade chemical compounds in crude oil for which there may be little value to high octane fuel components. The two acids mentioned above are the catalysts of choice as the process is not operated commercially, but each of them while producing a satisfactory alkylate for fuel blending has serious drawbacks. The use of HF presents a significant ecological hazard should it escape into the atmosphere, and the sulfuric acid process is very corrosive and energy consuming as it needs to be operated at below ambient temperatures in order to provide a satisfactory alkylate. Certain solid compositions with acidic properties have been found to catalyze this reaction as disclosed in the following Japanese patents.

In Hatakeyama et al Japanese Kokai Patent, SHO 61-183230, Aug. 15, 1986, fractions rich in 2,2,3-trimethylpentane are produced from butenes and isobutane by alkylation over a super strongly acidic zirconia catalyst obtained by contacting zirconium hydroxide or zirconium oxide with a solution containing sulfate radical, followed by roasting.

In Abstract No. 106: 216817b, CA Selects: Catalysis (Applied & Physical Aspects), Issue 13, Jun. 29, 1987, Ito et al, Jpn. Kokai Tokkyo Koho JP 61,242,641 {86,242,641], Oct. 28, 1986 is abstracted, disclosing catalysts for isobutane alkylation prepared by impregnating sulfate ion or its precursor-containing materials and rare earth metals or their compounds, e.g. lanthanum nitrate, on supports consisting of Group IVA or IVB metal hydroxides or oxides, followed by calcination and stabilization.

In the corresponding Ito et al Japanese Kokai Patent, SHO 61-242641, Oct. 28, 1986, application SHO 60-84515 filed Apr. 22, 1985, a solid acidic catalyst for alkylation of isoparaffin with olefin is disclosed. The catalyst is obtained by adding a rare earth element or its compounds, and sulfate radical or its precursor to a supporting member made of hydroxide or oxide of Group IV metals, followed by sintering at 400°–800° C., for stabilization. Hydroxide or oxide of at least one type of metals chosen from titanium, zirconium, hafnium, silicon, germanium and tin is used; particularly hydroxide or oxide of zirconium or titanium is preferred. Tantalum and cerium or their compounds are disclosed, as most desirable rare earths; praseodymium, neodymium, samarium and gadolinium are also disclosed.

In Hosoi et al Japanese Kokai Patent, HEI 1-24583 disclosure date Oct. 2, 1989, Application No. SHO 63-73409, Mar. 29, 1988, solid acid catalyst for alkylation is provided, using at least one type of metal containing metals of Group II-b, for example zinc or mercury, Group V-a, for example vanadium, niobium or tantalum, Group VI-a, for example chromium, molybdenum or tungsten, Group VII-a, for example manganese or rhenium, on a carrier consisting of oxides or hydroxides with Group III and/or Group IV metal hydroxides or its compounds and a sulfate radical or precursors of a sulfate radical. Sulfated zinc/zirconium hydroxides, chromium/zirconium hydroxides, vanadium/zirconium hydroxides, manganese/zirconium hydroxides, zinc/titanium hydroxides, zirconium/titanium hydroxides, zirconium/aluminum hydroxides are disclosed.

In Shimizu et al Japanese Kokai Patent HEI 1-245854, disclosure date Oct. 2, 1989, Application No. SHO 63-73410, Mar. 29, 1988, a solid acid catalyst for alkylation of isobutane by olefins is obtained by adding a sulfate or precursor thereof to a carrier comprising compound metal hydroxides or compound metal oxides of at least more than two kinds of metals selected from titanium, zirconium, silicon and tin. Sulfated zirconia/titania, zirconia/tin oxide, zirconium/silicon catalysts are disclosed.

Chemical Week, Nov. 25, 1987, on page 28, discloses superacids obtained by sulfating zirconium, titanium and iron oxides, as catalysts for alkylation of orthoxylene by styrene.

We have discovered that certain metal combinations when incorporated with the strongly acidic solid-acids, which are in one embodiment of the invention generated by treating zirconia with ammonium sulfate and then calcining at high temperatures, provide alkylation catalysts superior to that obtained by the use of the sulfated zirconia alone. That is to say that the alkylate produced by the modified sulfated zirconia has a higher proportion of 8-carbon compounds than that obtained when using only the sulfated zirconia. Concurrently the amount of light ends (5–7 carbon products) which arise from cracking the C-8 and higher fractions is reduced. Additionally the alkylation reaction can be carried out at room temperature to provide good yields of alkylate, thus eliminating the need for sub-ambient cooling and results in a more energy efficient operation. Furthermore these new catalysts provide a significantly higher percentage of the high octane trimethylpentanes within the 8-carbon fraction than one obtains with sulfated zirconia alone or with the traditional acid catalysts. The new composition of matter according to the invention comprises a sulfated and calcined mixture of (1) a support comprising an oxide or hydroxide of a Group IV-A element, (2) an oxide or hydroxide of molybdenum, and (3) an oxide or hydroxide of a metal selected from the group consisting of Group V-A metals, Group IV-A metals other than molybdenum, Group I-B metals, Group II-B metals, Group III-A metals, Group III-B metals, Group IV-B metals, and metals from the Lanthanide Series of the Periodic Table.

The solid super-acid catalyst is prepared by incorporating the desired metals (or ions) onto a sulfated zirconia or other support comprising an oxide or hydroxide of a Group IV-A element, by techniques known to those skilled in the art of catalyst preparation for example, the technique disclosed in Example 1 of U.S. Pat. No. 4,918,041 supra, wherein a composite of zirconia, iron and manganese is prepared, calcined and sulfated. Alkylate superior to that obtained by employing the solid super-acid support alone is realized when one of the metals (or metal ions) employed is molybdenum and the other metal comes from groups V-A (V, Nb, Ta), VI-A (Cr, Mo, W), I-B (Cu, Ag, Au), II-B (Zn, Cd, Hg), III-A (Sc, Y), III-B (B, Al, Ga, In, Tl), IV-B (Ge, Sn, Pb), or the Lanthanide Series of the Periodic Table. Metals from the Lanthanide Series which may be used are cerium, lanthanum, neodymium, praseodymium, samarium, gadolinium, and dysprosium of which cerium and lanthanum are preferred. Typical alkylation results are illustrated in Table I wherein it is recorded that the catalyst compositions of this invention provide higher concentrations of 8-carbon containing species and lower amount of $C_5$-$C_7$ cracked products than does a catalyst prepared from the super-acid zirconia support alone. However, not any two metal combination is effective in producing high 8-carbon selectivities in the alkylation reaction as illustrated by the data in Table II.

The data in Tables I & II were obtained from a semi-batch laboratory reactor operated as described below, but it is believed that the advantage provided by the catalysts of this invention can be obtained in other commercially appropriate reactor configurations. A small (300 ml) Parr reactor was charged with 20 gms. of dry catalyst and 50 mls. of isobutane. With stirring, a 15/1 feed of isobutane/butene-2 was added at the rate of 43 mls./hr for four hours. At the end of the addition the reactor was allowed to stir an additional hour. The product was withdrawn and analyzed by gas chromatography to determine the carbon number and isomer distributions which are reported in the tables.

The support upon which the metal is incorporated in this embodiment need not be entirely composed of sulfated zirconia. Mixtures of zirconia with other appropriate oxides such as the oxides from elements in Groups III-A & B, IV-A & B of the Periodic Table may be used. Mixtures of these oxides along with zirconia will, upon being impregnated with the appropriate metals and sulfated, provide superior solid-acid alkylation catalysts. For example, silica-zirconia, titania-zirconia, alumina-zirconia, hafnia-zirconia represent appropriate supports for sulfation and impregnation within the scope of this disclosure. Alternatively, other elements from Group IV-A may be used instead of zirconium.

Table I shows the superiority of the molybdenum/tungsten on sulfated zirconia catalysts of Runs 2 and 3, and of the molybdenum/erbium on sulfated zirconia catalyst of Run 4 to the sulfated zirconia catalyst of Run 1 and to the cobalt/molybdenum of sulfated zirconia catalyst of Run 5. Table II shows the inferiority of various metal combinations on sulfated zirconia (chromium/tungsten, iron/manganese, iron/chromium, cobalt/chromium, nickel/vanadium, cobalt/tungsten, nickel/chromium, nickel/molybdenum and nickel/tungsten), other than those claimed herein, to sulfated zirconia itself.

TABLE I

| | ALKYLATE COMPOSITION RUN NUMBER | | | | |
|---|---|---|---|---|---|
| | 1 | 2 | 3 | 4 | 5 |
| | METAL ION | | | | |
| | ZrO2/SO4 | Mo/W | Mo/W | Er/Mo | Co/Mo |
| C-3 | 0.05 | 1.02 | 0.48 | 0.31 | 0.25 |
| C-5 | 20.29 | 14.92 | 7.59 | 8.29 | 17.44 |
| C-6 | 9.86 | 7.18 | 4.21 | 5.31 | 8.24 |
| C-7 | 10.72 | 10.49 | 6.84 | 8.61 | 10.56 |
| C-8 | 48.94 | 62.78 | 70.78 | 68.80 | 52.98 |
| C-9 | 1.70 | 1.66 | 2.02 | 2.00 | 4.16 |
| C-10 | 3.60 | 0.83 | 1.58 | 1.42 | 1.84 |
| C-12 | 3.50 | 1.13 | 6.00 | 4.71 | 4.30 |
| >C-12 | 1.32 | 0.00 | 0.50 | 0.55 | 0.23 |

TABLE II

| | ALKYLATE COMPOSITION RUN NUMBER | | | | | | | | | | |
|---|---|---|---|---|---|---|---|---|---|---|---|
| | 6 | 7 | 8 | 9 | 10 | 11 | 12 | 13 | 14 | 15 | 16 |
| | ZrO2/SO4 | Cr/W | Fe/Mn | Fe/W | Fe/Cr | Co/Cr | Ni/V | Co/W | Ni/Cr | Ni/Mo | Ni/W |
| C-3 | 0.05 | 20.57 | 0.11 | 2.16 | 0.40 | 0.42 | 0.39 | 0.42 | 0.48 | 0.30 | 0.04 |
| C-5 | 20.29 | 1.35 | 31.92 | 1.06 | 37.76 | 27.42 | 27.32 | 37.14 | 37.32 | 29.13 | 20.71 |
| C-6 | 9.86 | 2.44 | 13.78 | 0.95 | 13.32 | 10.44 | 9.41 | 11.88 | 12.37 | 10.36 | 9.14 |
| C-7 | 10.72 | 26.06 | 9.81 | 1.53 | 10.04 | 10.45 | 9.60 | 10.94 | 10.33 | 10.61 | 8.82 |
| C-8 | 48.94 | 36.22 | 34.93 | 38.22 | 31.69 | 43.71 | 46.23 | 34.05 | 34.56 | 43.30 | 1.31 |
| C-9 | 1.70 | 2.70 | 1.66 | 4.73 | 3.52 | 4.05 | 3.60 | 3.24 | 3.28 | 1.88 | 2.93 |
| C-10 | 3.60 | 1.46 | 3.61 | 3.07 | 1.64 | 1.40 | 1.37 | 1.01 | 0.82 | 1.27 | 2.59 |
| C-12 | 3.50 | 9.13 | 2.56 | 23.04 | 1.59 | 2.09 | 2.06 | 1.31 | 0.82 | 2.72 | 1.88 |
| C->12 | 1.32 | 0.05 | 1.22 | 3.14 | 0.03 | 0.02 | 0.00 | 0.00 | 0.00 | 0.13 | 0.00 |

We claim:

1. A composition of matter comprising a sulfated and calcined mixture of (1) a support comprising an oxide or hydroxide of a Group IV-A element, (2) an oxide or hydroxide of molybdenum, and (3) an oxide or hydroxide of a metal selected from the group consisting of Group V-A metals, Group VI-A metals other than molybdenum, Group I-B metals, Group II-B metals, Group III-A metals, Group III-B metals, Group IV-B metals, and metals from the Lanthanide Series of the Periodic Table.

2. Composition according to claim 1 wherein said metal is vanadium, niobium or tantalum.

3. Composition according to claim 1 wherein said metal is chromium or tungsten.

4. Composition according to claim 1 wherein said metal is copper, gold or silver.

5. Composition according to claim 1 wherein said metal is zinc, cadmium or mercury.

6. Composition according to claim 1 wherein said metal is scandium or yttrium.

7. Composition according to claim 1 wherein said metal is boron, aluminum, gallium, indium or thallium.

8. Composition according to claim 1 wherein said metal is germanium, tin or lead.

9. Composition according to claim 1 wherein said metal is cerium, lanthanum, neodymium, praseodymium, samarium, gadolinium and dysprosium.

* * * * *